Figure 1:
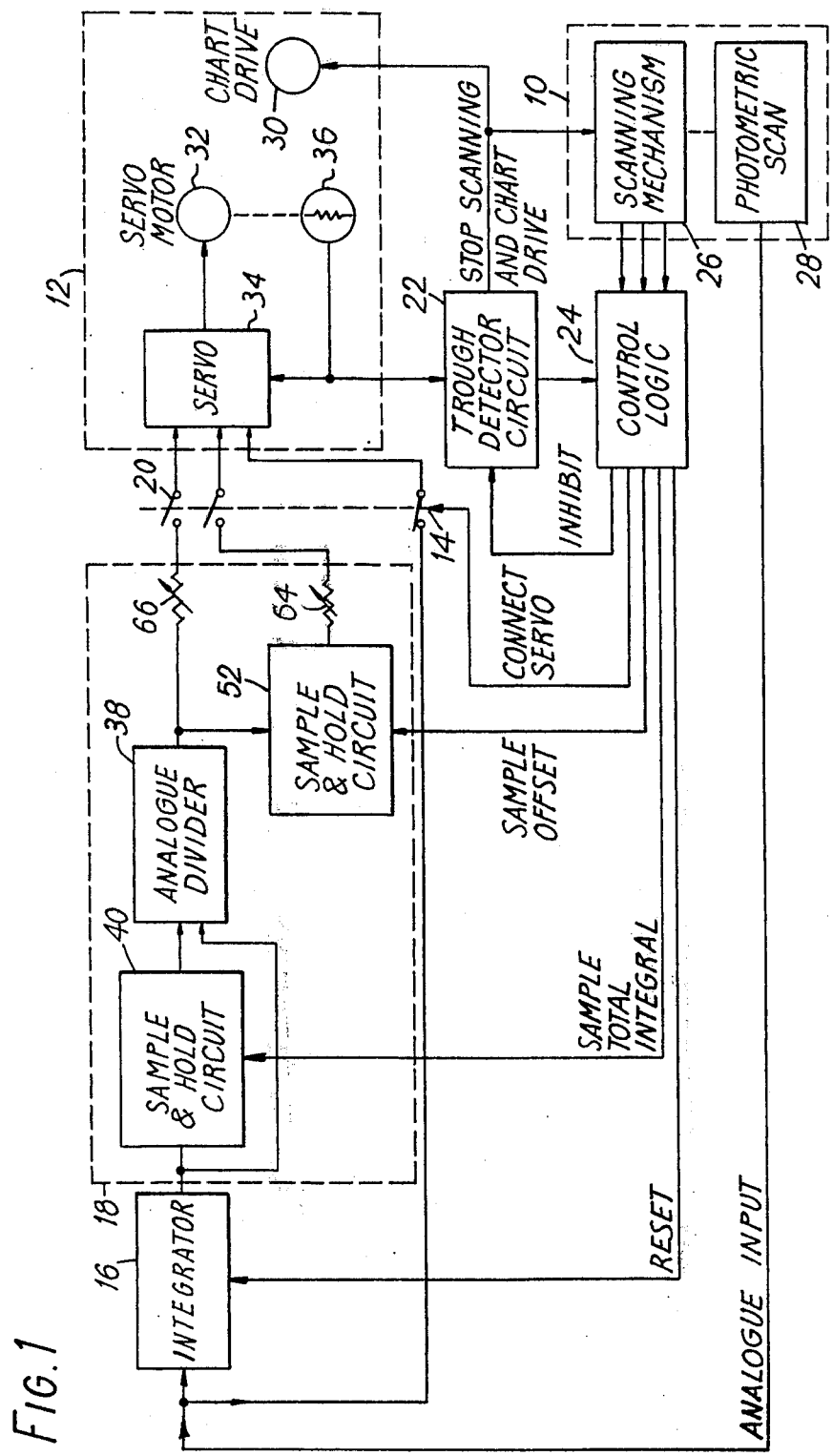

United States Patent [19]
Hambleton et al.

[11] 3,965,477
[45] June 22, 1976

[54] AUTOMATIC GRAPHING APPARATUS

[76] Inventors: James Hambleton; Peter Frank Davies; Philip Edward Harley; Gianfranco Corsi, all of 8, Princesway, Team Valley, Durham, England

[22] Filed: Apr. 4, 1974

[21] Appl. No.: 457,848

[30] Foreign Application Priority Data
Apr. 9, 1973 United Kingdom............... 16836/73

[52] U.S. Cl........................... 346/33 A; 235/151.35; 346/13; 346/62; 356/105
[51] Int. Cl.²........................................... G01D 1/04
[58] Field of Search..................... 346/13, 33 A, 62; 235/151.35, 151.3, 183; 356/105, 202, 203

[56] References Cited
UNITED STATES PATENTS

| | | | |
|---|---|---|---|
| 2,134,581 | 10/1938 | Rowell | 346/62 X |
| 3,051,898 | 8/1962 | Eynon | 346/62 X |
| 3,573,843 | 4/1971 | Solley | 346/62 |
| 3,681,774 | 8/1972 | Harris et al. | 346/62 |
| 3,706,877 | 12/1972 | Clifford | 235/151.35 |

*Primary Examiner*—Joseph W. Hartary
*Attorney, Agent, or Firm*—Alfred H. Rosen; Frank A. Steinhilper

[57] ABSTRACT

Apparatus for producing a graph of a function represented by a varying analogue input signal supplied to the apparatus, comprising display means adapted to display in a graphing operation the graph of the function, calculating means adapted to receive the analogue input signal and to calculate the value of a parameter of the function, and control means operable to interrupt the operation of the display means at preselected points in the graphing operation and to cause the display means to display the value calculated by the calculating means and thereafter to resume the graphing operation.

7 Claims, 9 Drawing Figures

AUTOMATIC GRAPHING APPARATUS

This invention relates to automatic graphing apparatus.

It is often desirable to produce a graph of a function represented by a varying analogue signal and to record at appropriate points on the graph representations of some parameter of the function. For example, in apparatus for producing, in response to a voltage input derived from a photometric scan of an electrophoresis strip obtained in an electrophoresis evaluation of a protein sample, a graph displaying the light absorbence profile of the strip, it is desirable to record also values proportional to the area under each peak of the graph, those areas being proportional to the masses of individual proteins separated by the electrophoresis process. Hitherto, this has only been possible with apparatus such as two-pen graphical systems, which are relatively complex and expensive.

According to this invention there is provided apparatus for producing a graph of a function represented by a varying analogue input signal supplied to the apparatus, comprising display means adapted to display in a graphing operation the graph of the function, calculating means adapted to receive the analogue input signal and to calculate the value of a parameter of the function, and control means operable to interrupt the operation of the display means at preselected points in the graphing operation and to cause the display means to display the value calculated by the calculating means and thereafter to resume the graphing operation.

Preferably the display means is a pen recorder comprising a pen, chart drive means for moving a chart past the pen so that the pen leaves a trace on the chart, pen drive means for moving the pen in a direction transverse to the direction of movement of the chart in response to an input signal, and there are provided means for supplying the said analogue input signal or the pen drive means during movement of a chart by the chart drive means, the control means being adapted to stop movement of the chart at the preselected points and to connect the calculating means to the pen drive means whilst the chart is stationary so that the pen provides on the chart an indication of the calculated value of the said parameter.

Suitably, there is provided a trough detector circuit adapted to detect the occurrence of a minimum point in the analogue input signal to the apparatus and to supply a signal to the control means at each such occurrence to cause interruption of the graphing operation.

Figure 2:
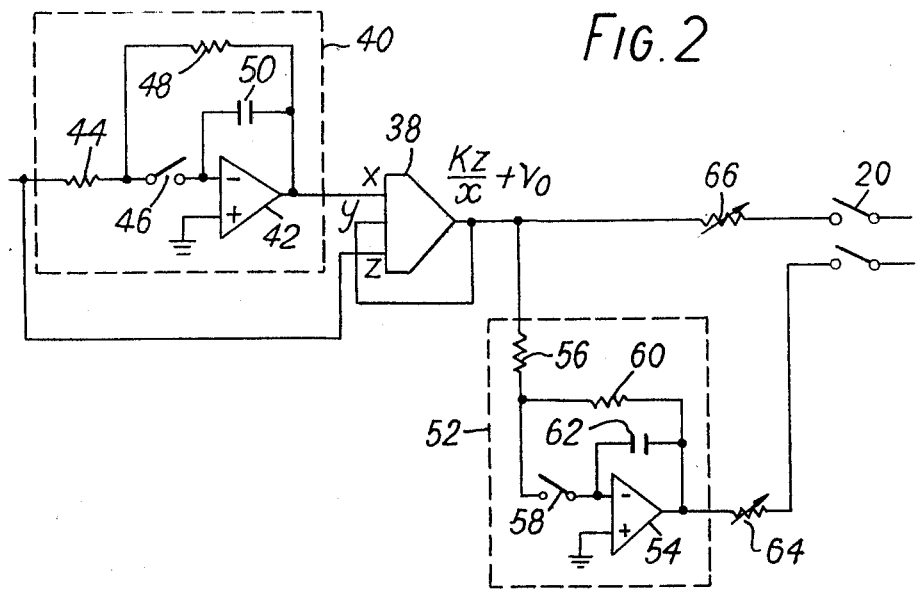
Figure 4:
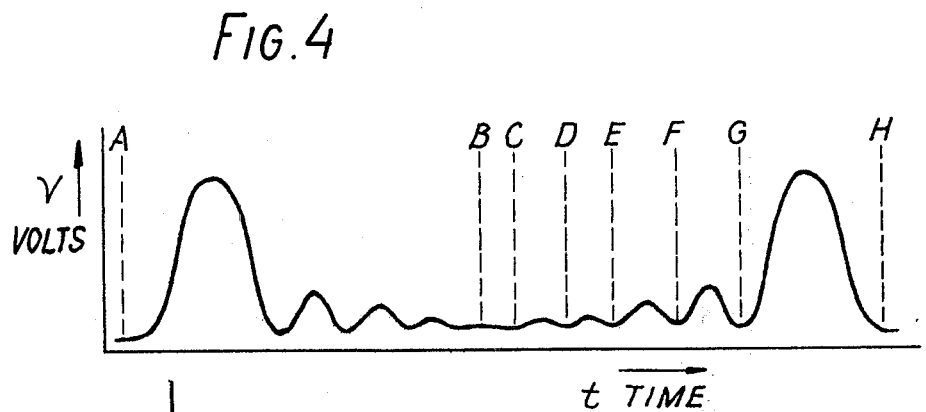
Figure 5:
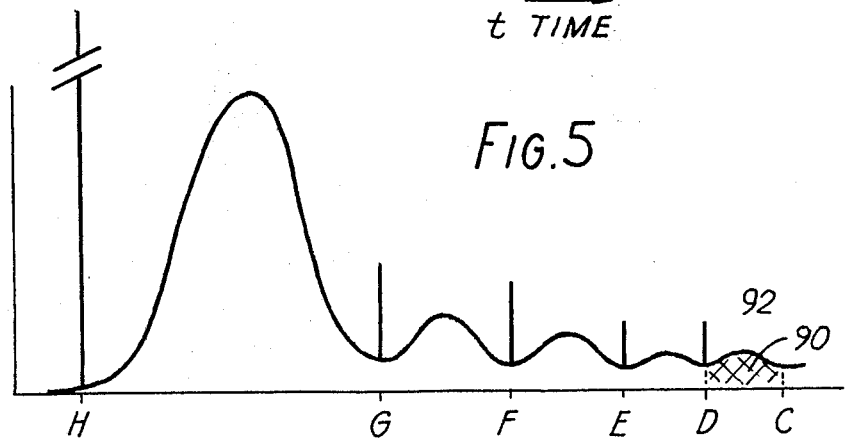
Figure 3:
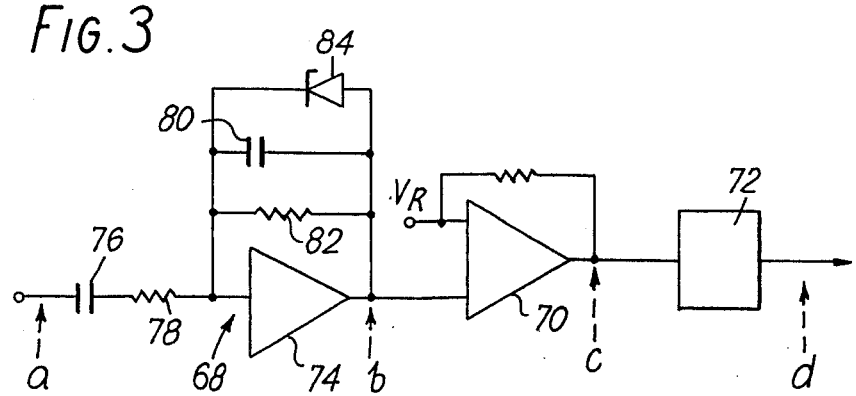
Figure 3A:
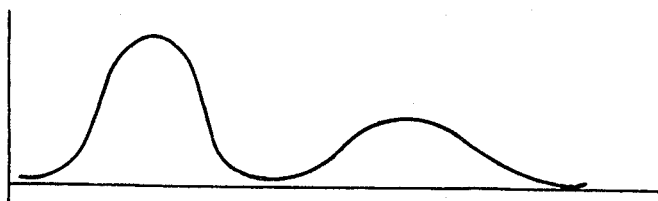
Figure 3B:
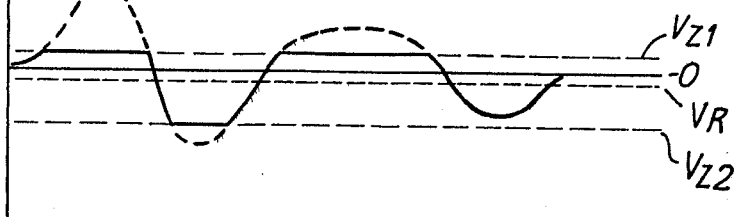

The invention will now be described, by way of example, with reference to the accompanying drawings, in which:

FIG. 1 is a block diagram of automatic graphing apparatus constructed in accordance with the invention, FIG. 2 is a diagram of a percentage computing circuit and associated circuitry forming part of the apparatus of FIG. 1, FIG. 3 is a diagram of a trough detector circuit forming part of the apparatus of FIG. 1, FIGS. 3a to 3d illustrate the wave forms of voltages appearing in operation at points a to d of the circuit of FIG. 3, FIG. 4 shows a typical absorbence profile providing an input to the apparatus of FIG. 1, and FIG. 5 shows a typical graph produced by the apparatus of FIG. 1.

As shown in FIG. 1, the apparatus includes photometric scanning apparatus 10, adapted to scan an electrophoresis strip and to generate an output voltage proportional to the light absorbence of the strip at any instant in the scanning operation, a servo-driven pen recorder 12 adapted to receive through switch 14 the output voltage of scanning apparatus 10 and to produce on a paper chart a graph of the voltage with respect to time, an integrator 16 adapted to generate a time integral of the output voltage of the scanning apparatus 10, a percentage computing circuit 18 adapted to receive the output of the integrator 16 and to calculate the area under each peak of the graph as a percentage of the total area under the graph, the result being supplied to the pen recorder 12 through switch 20, a trough detector circuit 22 adapted to sense troughs (i.e. points of minimum voltage) on the graph, and control logic 24 adapted to control the sequence of operations of the other components of the apparatus.

The scanning apparatus 10 comprises a scanning mechanism 26 operable to effect relative movement between a photometric scanning head and an electrophoresis strip, and photometric means 28 for measuring the light absorbence of the strip at each instant during the scan and to generate an output voltage proportional to the light absorbence. The photometric means may be of any suitable well-known form. The scanning mechanism 26, is operable to effect relative movement between the scanning head and electrophoresis strip in one direction at constant speed followed immediately by a reverse scan at the same constant speed in the opposite direction, so that the variation with time of the output voltage of the photometric means is symmetrial, for example as shown in FIG. 4. Control signals derived from the scanning mechanism 26, indicating for example the beginning and end of each of the forward and reverse scans, are supplied to the control logic 24.

The pen recorder 12 includes a chart drive mechanism 30 for moving chart paper past a single recording pen driven by a motor 32 controlled by a servo-mechanism 34. The servo-mechanism is of the self-balancing type including a feedback potentiometer 36 having an adjusting member which is driven by motor 32 to maintain the voltage output of the potentiometer equal to the input voltage to the servo-mechanism.

The integrator 16 is a conventional analogue integrator, having an output proportional to the accumulated integral with respect to time of the input voltage applied to it. The integrator can be reset by a control signal from the control logic 24.

The percentage computing circuit 18, which is shown in more detail in FIG. 2, comprises an analogue divider 38, formed in well-known manner by placing a suitable feedback network around a monolithic integrated circuit multiplier. The z-input to multiplier 38 is provided by the output of integrator 16. The x-input to the multiplier 38 is provided by the voltage stored in a "sample and hold" circuit 40, which consists of an operational amplifier 42 (FIG. 2). The output of integrator 16 can be supplied to the inverting input of the amplifier through a resistor 44 and relay contacts 46, the non-inverting input being earthed. A resistor 48 is connected between the output of amplifier 42 and the junction of resistor 44 and relay contacts 46, and a capacitor 50 is connected between the output of the amplifier and its inverting input so that when relay contacts 46 are opened the output voltage of the amplifier is retained on capacitor 50. The output of the amplifier then remains at the same value, equal to the output of the integrator at the time when relay contacts 46 opened but of the opposite polarity. The output of divider 38 at any subsequent instant will thus be equal to the output of integrator 16 at that instant divided by the output of the integrator corresponding to the value held by circuit 40 and mulitplied by an arbitrary constant factor K, plus a constant offset voltage VO whose value is characteristic of the particular integrated circuit 38.

To correct for the offset voltage of divider 38, a second sample and hold circuit 52 is connected to the output of divider 38. Circuit 52 is similar to sample and hold circuit 42, consisting of an operational amplifier 54, the inverting input of which is connected through resistor 56 and relay contacts 58 to the output of divider 38, a resistor 60 connected between the output of amplifier 54 and the junction of resistor 56 and contacts 58 and a capacitor 62 connected between the output and inverting input of amplifier 54. Contacts 58 are closed, by a signal from control logic 24, whenever integrator 16 is reset. Since the output of the integrator, and therefore the z-input to divider 38, is then zero the output of the divider is equal to its offset voltage. The output of amplifier 54 is thus equal to the offset voltage but of opposite polarity, and after contacts 58 are re-opened this output is maintained by capacitor 62. The output is supplied through variable resistor 64 and relay contacts 20 to the servo 34 so that, during subsequent supply of the output of divider 38 to the servo, the offset voltage is subtracted from the output of the divider. Variable resistor 64 enables adjustment of the offset compensation provided by circuit 52.

The output of analogue divider 38 is supplied to servo 34 through relay contacts 20 and a variable resistor 66, which allows the output of the pen recorder for a given output of divider 38 to be adjusted, to compensate for variations in the arbitrary constant K of divider 38 between different instruments so that the same pre-calibrated graph paper can be used in different instruments.

Figure 3C:
Figure 3D:
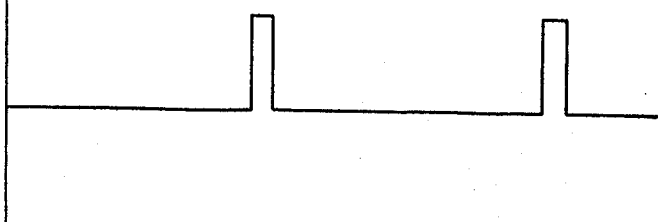

As shown in FIG. 3, the trough detector circuit 22 comprises a differentiator 68, the output of which is connected to a Schmitt trigger circuit 70, and an edge-triggered monostable circuit 72 which receives the output of the Schmitt trigger. The differentiator 68 is of conventional form, comprising an operational amplifier 74, to which the input is supplied through a capacitor 76 and resistor 78, and which has a feedback circuit consisting of a capacitor 80 and resistor 82 connected in parallel. A zener diode 84 is connected across capacitor 80 to limit the charge retained on capacitor 80 during peaks of the output waveform and to hold the amplifier 74 out of saturation during troughs of the output waveform. Thus, in response to an input voltage having a waveform such as that shown in FIG. 3a, the differentiator 68 provides an output, shown in solid line in FIG. 3b, consisting of the input waveform differential with respect to time, and cut off at the voltage levels $V_{Z1}$ and $V_{Z2}$ determined by the zener diode 84. The output waveform therefore passes through zero at the instants at which the input waveform passes through maximum or minimum values, i.e. at the peaks and troughs of the input waveform. The Schmitt trigger 70 is so arranged that it produces an output voltage, as shown in FIG. 3c, when the output of the differentiator 68 falls below the reference voltage $V_R$ of the Schmitt trigger. The output of the Schmitt trigger circuit is thus a square wave, the falling edges of which occur at instants close to the occurrence of troughs in the input waveform to the trough detector circuit. The edge triggered monostable circuit 72 is arranged to provide an output pulse at the occurrence of each falling edge of the output waveform of the Schmitt trigger. The trough detector circuit 22 thus provides an output pulse practically co-incident with the occurrence of each trough of the input waveform to the circuit.

The time constants of the differentiator 68 and the reference voltage level of Schmitt trigger circuit 70 are chosen so that the minimum slope of the input waveform which is detected by the circuit 22 is sufficiently small to ensure accurate detection of the position of the troughs, whilst being large enough to eliminate false triggering of the circuit by low frequency noise in the input waveform. To eliminate the effects of high frequency noise in the output from the photometric scanner 28, the input to trough director circuit 22 is taken not from the scanner 28 but from the feedback potentiometer 36 of the servo-mechanism 34. Because of the relatively slow response of the servomechanism, it performs the function of a low pass filter, providing a signal to the trough detector circuit 22 which corresponds to the input signal from scanner 28 but devoid of high frequency noise.

The operation of the apparatus will now be described with reference to FIG. 4, which shows a typical output voltage from the photometric scanner 28. As the scan of a specimen band commences, at time A, the integrator 16 is reset by a control signal from control logic 24. Between times A and C the servo-mechanism 34 and chart drive are disabled and the trough detector 22 is inhibited so that it produces no output signals.

As the scan progresses from A to B, integrator 16 accumulates at its output the total time integral under the curve between A and B. At time B a command is given to the sample and hold circuit 40 so that the value of the total integral is stored by the circuit as described above. This value, which is proportional to the total mass of material in the specimen band, is stored by circuit 40 until the beginning of a subsequent scan of the next specimen band.

At time C integrator 16 is reset by a signal from control logic 24. At the same time a signal is given to sample and hold circuit 52 so that it stores the offset voltage of divider 38 as described above. Between times C and H, i.e. during the reverse scan of the specimen band, the servo-mechanism 34, chart drive 30 and trough detector 22 are enabled.

Between times C and D, relay contacts 20 are open, and contacts 14 are closed to connect the output of scanner 28 to the servo-mechanism 34. The pen recorder 12 therefore draws out the absorbence profile of the specimen band, as shown in FIG. 5, which shows the graph produced by the apparatus (the relative movement between pen and chart in FIG. 5 being from right to left of the Figure). At the same time, integrator 16 accumulates the time integral corresponding to the area under the graph shown hatched at 90 in FIG. 5, which represents the mass of material in the specimen band scanned between times C and D.

At time D, the trough detector circuit 22 detects a minimum in the feedback signal from potentiometer 36, indicating a minimum in the input waveform, and supplies a signal to control logic 24, which causes the scanning mechanism 26 and the chart drive 30 to stop. At the same time, contacts 14 are opened and contacts 20 are closed, to connect the output of the percentage computing circuit 18 to the servo-mechanism 34. The pen of recorder 12 therefore draws on the stationary chart paper a vertical line 92 (see FIG. 5) whose height is proportional to the output of the percentage computing circuit, and therefore indicates the mass of material on the specimen band scanned between times C and D as a fraction of the total mass of material in the band. After a delay sufficient to allow the pen to draw the vertical line, contacts 20 are opened and contacts 14 closed, so that the output of scanner 28 is re-applied to servo-mechanism 34 and the pen returns to the corresponding point of the graph. Integrator 16 is meanwhile reset. The scanning mechanism 26 and chart drive 30 are then re-started, so that the pen continues to draw the absorbence profile. Since the chart paper is stationary as vertical line 92 is drawn, the graph shows no discontinuity in the absorbence profile.

The sequence of events occurring between times C and D is repeated between times D and E, E and F, F and G, and G and H.

The graph produced by the apparatus thus consists, as shown in FIG. 5, of a curve representing the absorbence profile of the specimen band scanned, on which are superimposed vertical lines indicating, as a percentage of the total protein mass, the mass of separated protein represented by each peak of the curve, each line being adjacent the corresponding peak of the curve.

What we claim is:

1. Apparatus for producing a graph of a function represented by a varying analogue input signal, comprising:
   display means for tracing out in a graphing operation the graph of said function as said input signal is supplied to the apparatus;
   calculating means including an integrator for providing an output proportional to the time integral of said input signal as it is supplied to the apparatus;
   input means for supplying said input signal simultaneously to the display means and calculating means;
   said input means including first switch means between said input means and said display means;
   second switch means through which said calculating means is connected to said display means to selectively supply the said output thereto;
   a trough detector circuit;
   means for supplying to the trough detector circuit a signal derived from said input signal;
   the trough detector circuit detecting the occurrence of a minimum point in the input signal and supplying a control signal at each such occurrence;
   control means connected to the display means, trough detector circuit and said first and second switch means, the control means, in response to a control signal from the trough detector, acting to actuate said first and second switch means to disconnect the input signal from the display means, and to connect the calculating means to the display means, thereby to interrupt the graphing operation and cause the display means to display a value indicative of said output of the calculating means, and thereafter to cause the display means to resume the graphing operation, whereby the display means displays both the graph of said function and values indicative of the time integral of said function between successive interruptions of the graphing operation.

2. Apparatus as claimed in claim 1, in which the display means is a pen recorder comprising a pen, chart drive means for moving a chart past the pen so that the pen leaves a trace on the chart, and pen drive means for moving the pen in a direction transverse to the direction of movement of the chart in response to an input signal, the input means supplying the said analogue input signal to the pen drive means during movement of a chart by the chart drive means, the control means being adapted to stop movement of the chart at the preselected points and to connect the calculating means to the pen drive means whilst the chart is stationary so that the pen provides on the chart an indication of the calculated value of the said parameter.

3. Apparatus as claimed in claim 1, in which the said input signal is a voltage signal derived from a repeated photometric scan of a single electrophoresis sample, the integrator calculating during the first scan the total time integral of the signal, and the calculating means includes a sample and hold circuit connected to the integrator for storing the output of the integrator after the first scan and a computing circuit producing at each interruption of the graphing operation an output proportional to the ratio between the instantaneous output of the integrator and the value stored in the sample and hold circuit.

4. Apparatus as claimed in claim 3, in which the computing means includes an analogue divider the output of which is equal to a value proportional to the said ratio plus a constant offset value, and a second sample and hold circuit connected to the analogue divider so as to receive and store the said offset value which appears at the output of the divider immediately after the integrator has been reset so that the integrator output is zero, the second sample and hold circuit being so connected to the display means that the offset value is subtracted from the output of the analogue divider supplied to the display means on interruption of the graphing operation.

5. Apparatus as claimed in claim 1, in which the trough detector circuit comprises a differentiator adapted to receive the said signal and to generate a signal proportional to the derivative with respect to time of the said signal, and a trigger circuit adapted to provide an output signal when the derivative signal passes through a present minimum value.

6. Apparatus as claimed in claim 5, in which the trigger circuit comprises a Schmitt trigger circuit operable to generate a square wave the rising and falling edges of which correspond to the occurrence of peaks and troughs respectively of the analogue input signal, and an edge-triggered monostable circuit connected to the Schmitt trigger circuit so as to provide an output pulse in response to each falling edge of the square wave.

7. Apparatus as claimed in claim 1, and including display means in the form of a pen recorder of the kind in which the pen is moved by a servo-mechanism including a feedback potentiometer from which is derived an output signal of magnitude dependent on the deflection of the pen, in which the input to the trough detector circuit is derived from the output signal of the feedback potentiometer.

* * * * *